US008113061B2

(12) United States Patent
Bailey et al.

(10) Patent No.: US 8,113,061 B2
(45) Date of Patent: Feb. 14, 2012

(54) MATERIALS TESTING (75) Inventors: Robin S. Bailey, Redcar (GB); Alan McNicol, Great Ayton (GB); John Carroll, Stockton-on-Tees (GB)

(73) Assignee: Brunob II B.V., Arnhem (NL)

( * ) Notice: Subject to any disclaimer, the term of this patent is extended or adjusted under 35 U.S.C. 154(b) by 138 days.

(21) Appl. No.: 10/559,282

(22) PCT Filed: Jun. 3, 2004

(86) PCT No.: PCT/GB2004/002338
§ 371 (c)(1),
(2), (4) Date: Jun. 1, 2006

(87) PCT Pub. No.: WO2004/109258
PCT Pub. Date: Dec. 16, 2004

(65) Prior Publication Data
US 2006/0243057 A1     Nov. 2, 2006

Related U.S. Application Data

(60) Provisional application No. 60/477,060, filed on Jun. 10, 2003.

(30) Foreign Application Priority Data

Jun. 5, 2003  (GB) .................................. 0312917.8

(51) Int. Cl.
*G01N 3/00*     (2006.01)
(52) U.S. Cl. ........................................................ 73/788

(58) Field of Classification Search ............... 73/788, 73/579
See application file for complete search history.

(56) References Cited

U.S. PATENT DOCUMENTS

| | | | |
|---|---|---|---|
| 2,723,554 A | | 11/1955 | Berlin et al. |
| 4,567,774 A | | 2/1986 | Manahan et al. |
| 4,640,120 A | | 2/1987 | Garritano et al. |
| 4,899,581 A | | 2/1990 | Allen et al. |
| 5,280,717 A | * | 1/1994 | Hoseney et al. ............. 73/54.22 |
| 5,569,918 A | * | 10/1996 | Wang ............................. 850/53 |
| 5,633,467 A | * | 5/1997 | Paulson ........................ 73/800 |
| 5,789,681 A | * | 8/1998 | Angley et al. ................. 73/803 |
| 5,869,751 A | * | 2/1999 | Bonin ............................. 73/105 |
| 5,904,658 A | * | 5/1999 | Niederauer et al. .......... 600/587 |

(Continued)

FOREIGN PATENT DOCUMENTS

EP     1158290     11/2001

(Continued)

OTHER PUBLICATIONS

International Search Report dated Aug. 16, 2004 for PCT/GB2004/002338.

*Primary Examiner* — Lisa Caputo
*Assistant Examiner* — Octavia Davis
(74) *Attorney, Agent, or Firm* — Jones Day (57) ABSTRACT

Methods of and apparatus for testing a material are described. The testing involves providing a material across a region of a support member which is arranged to define an opening and moving a force applying device relative to the material to apply a force to the material. The force applying device moves towards, passes into and/or passes through the opening prior to, during or after applying the force to the material.

35 Claims, 6 Drawing Sheets

U.S. PATENT DOCUMENTS

| | | | |
|---|---|---|---|
| 5,977,783 A * | 11/1999 | Takayama et al. | 324/754 |
| 6,196,866 B1 * | 3/2001 | Gaschke | 439/482 |
| 6,736,017 B2 * | 5/2004 | Mansky | 73/862.046 |
| 6,769,292 B2 * | 8/2004 | Mansky et al. | 506/12 |
| 6,805,011 B2 * | 10/2004 | Tegtmeier et al. | 73/788 |
| 6,852,627 B2 * | 2/2005 | Sinha et al. | 438/687 |
| 6,857,309 B2 * | 2/2005 | Mansky | 506/12 |
| 6,928,877 B2 * | 8/2005 | Carlson et al. | 73/579 |
| 6,936,471 B2 * | 8/2005 | Hajduk et al. | 436/2 |
| 6,998,705 B2 * | 2/2006 | Noguchi | 257/701 |
| 7,013,709 B2 * | 3/2006 | Hajduk et al. | 73/37 |
| 2003/0037620 A1 | 2/2003 | Mansky | |
| 2003/0054740 A1 | 3/2003 | Mansky | |

FOREIGN PATENT DOCUMENTS

JP     2003-220668     8/2003

* cited by examiner

XY Translation Stage

MATERIALS TESTING

Cross Reference to Related Applications

This application is the National Phase application of International Application No. PCT/GB2004/002338, filed Jun. 3, 2004, which designates the U.S. and was published in English, which claims priority to U.S. Provisional Application No. 60/477,060, file Jun. 10, 2003. Both applications, in their entirety, are incorporated herein by reference.

This invention relates to materials testing and particularly, although not exclusively, provides a method of testing a material and apparatus therefor.

There are numerous known methods of testing materials either as one-off samples or with a multiplicity of materials to be tested in an array. An example of an instrument for high-throughput measurement of material physical properties is described in EP 1 158 290 A (Symyx). Disadvantageously, many known methods simply provide "pass/fail" results rather than any significant quantitative data. Additionally, in some cases, very expensive and complex apparatus is used.

It is an object of the present invention to address problems associated with materials testing.

According to a first aspect of the invention, there is provided a method of testing a material, the method comprising:
(a) providing a material to be tested (hereinafter "test material") across a region of a support member which is arranged to define an opening;
(b) moving a force applying means relative to said test material to apply a force to said material; wherein said force applying means moves towards, passes into and/or passes through said opening prior to, during or after applying said force to said test material.

Said method preferably includes recording the force applied to said test material or a parameter relating to the force applied by said force applying means. The method may simply comprise assessing whether said test material passes or fails a test in which case only a single value for force applied may be recorded. The force may be measured to an accuracy of at least 5 mN, preferably at least 2 mN, more preferably at least 1 mN. Suitably, however, a multiplicity, preferably at least 10, more preferably at least 100, typically 500-1000, values for the force applied to said test material are recorded at different times during the testing of said material. Preferably, data relating to the force applied is recorded in a database, suitably under the control of a computer. Preferably, said computer controls the movement of said force applying means relative to said test material.

Preferably, the method involves said force applying means applying a force that deforms the test material. Preferably, data relating to the deformation of the test material is recorded in said database. Preferably, said data is related to the distance travelled by the force applying means relative to the test material. The distance travelled may be measured to an accuracy of at least 10 µm, preferably to at least 5 µm, more preferably to at least 2 µm. Preferably, a multiplicity, more preferably at least 10 values for the distance travelled are recorded at different times during the testing of said material. Preferably, values for the force applied and distance travelled are taken substantially concurrently during the method.

Movement of the force applying means relative to the test material preferably involves movement in the direction of a z axis that is perpendicular to an x-y plane in which the test material is generally arranged. Preferably, movement of the force applying means relative to the test materials involves vertical movement. Preferably, the method involves moving the force applying means to apply said force to said material. Said force applying means preferably moves downwardly. Preferably, said test material is stationary (except for any movement, e.g. deformation, caused by said force applying means) during application of said force. Preferably, said force applying means moves in the direction of a z axis as described (e.g. vertically) during application of said force and preferably, is only moved vertically during application of said force (i.e. there is substantially no movement of said force applying means in an x-y plane which is perpendicular to said z axis (e.g. no horizontal movement) during application of said force).

The method may involve moving the test material to a position in which said force applying means may apply said force. Said test material is preferably moved in the x-y direction, suitably in a substantially horizontal plane. Said test material is suitably moved in the method so that the force applying means is directly above the region of the support member which is arranged to define said opening. Preferably, a z axis (e.g. a vertical axis) of said force applying means (which axis defines the direction in which the force applying means moves relative to the test material) is substantially in line with the centre of the region which is arranged to define said opening so that when said force applying means passes through the opening it passes substantially centrally through the opening. Movement of the test material to said position described is preferably under the control of a computer. The positioning of the test material in the desired position is described in more detail hereinafter.

Preferably, said force applying means comprises a probe (which is preferably elongate and has its axis of elongation extending in the z direction (e.g. vertically) in which it is arranged to move) which moves (preferably in said z direction, e.g. substantially vertically) in the method and directly contacts said test material to apply said force thereto. Thus, the method preferably does not involve said force applying means applying said force via an intermediate member (e.g. a membrane) positioned between the force applying means, for example said probe, and said test material.

The method may involve constructing a force vs. extension relationship (e.g. graph) for the test material. The method may involve constructing a tensile stress vs. tensile strain relationship (e.g. graph) for the test material.

Said support member preferably defines a receptacle for containing the test material and a region which is arranged to define said opening. Said opening may be positioned centrally within the receptacle, preferably in a lower wall of the receptacle. More than one opening may be positioned within the receptacle, each being sufficiently remote from the periphery of the receptacle and from each other to ensure measurements are not affected by edge effects.

In one embodiment of the method, the test material may be arranged across a region of the support member which defines a said opening. This arrangement may be used when the properties of the test material are such that it does not sag into the opening during its formation and/or prior to it being tested, to any detrimental extent. Thus, in this case, the opening is unfilled prior to initiating movement of the force applying means. In another embodiment, the opening may be closed, for example by a plug means, prior to the test material being tested. The method of closing may involve packing a filler material, suitably a low friction particulate material (e.g. lightly sintered PTFE) into the opening. The filler material is arranged to contact the test material and prevent it sagging into the opening but it is sufficiently friable to disintegrate under a small load. Thus, the plug means, during testing of a test material, will disintegrate by force applied to it. In one instance, the force applying means is placed in direct contact with the plug means and applies force to the test material through the intermediary of the remains of the plug means. In another instance, force is applied to the plug means through displacement of the test material as it is deformed and enters the opening in response to force applied to it by the force applying means. The presence of the plug means is found to have negligible effect on force measurements.

In a first embodiment, said test material may be preformed, for example it may comprise a film, and the method may include the step of selecting said preformed test material and positioning it across said region of said support member. Preferably, the test material is clamped in position, suitably between two clamp plates, one of which incorporates said support member. A plurality of different test materials, for example films, may be clamped between clamp plates in which a plurality of openings may be arranged. The force applying means may then be moved to address each test material associated with an opening, in order to apply a force to the test material. The method described may be useful for test materials that are reasonably robust so that they can be handled with little detriment.

In a second embodiment, the method may involve forming the test material in situ. In this case, a precursor of the test material may be selected and contacted with said support member; said test material, which is suitably in a different physical form compared to said precursor, may then be formed. For example, said test material may be a film that is formed from a precursor that is suitably a flowable material and may be a liquid, a viscous fluid, a gel (or the like), a suspension or a free flowing solid material. Said precursor may be dispensed by any suitable means. For example, it could be dispensed using ink jet printer technology or by sputtering. Said precursor may be cast on said support member and a solvent removed thereby to form the film. The precursor may include at least first and second components that are involved in the formation of the test material. In a series of tests, the identity, and/or amounts of the first and second components may be varied; and/or the processes to which the first and second components may be subjected may be varied; and/or the identity and/or amounts of other components may be varied with a view to affecting the properties of the test material formed. Advantageously, formation of test materials in situ eliminates the need to handle (and risk damaging) test materials and the method can be used to test brittle material that could not be tested by other methods.

The second embodiment described represents another aspect of the invention. Thus, the invention extends to a method of testing a test material, the method comprising:
(a) selecting a precursor of said test material:
(b) contacting said precursor with a support member and forming said test material on the support member across a region of the support member which is arranged to define an opening;
(c) moving a force applying means relative to said test material;
(d) recording the force applied or a parameter relating to the force applied to said test material by said force applying means.

Step (c) of the method preferably comprises moving a force applying means relative to said test material to apply a force to said material, wherein said force applying means moves towards, passes into and/or passes through said opening prior to, during or after applying said force to said test material.

Said method of the first aspect may be a method of puncture testing, impact testing or adhesion testing.

In puncture testing, the method suitably involves moving said force applying means relative to the test material so that said force applying means penetrates the test material. After penetrating the material, said force applying means may pass into the opening. Before penetration, said force applying means is preferably spaced, for example in the direction of a z axis as described (e.g. vertically spaced), from said opening.

In puncture testing, a film is suitably supported on said support member, for example within a well, and the support member is arranged to define a said opening. In a preferred embodiment, the film is formed in situ in the well as described above. The method may involve determining the thickness of the film. This may be carried out using the force applying means. For example, the force applying means may be used to contact the film at a position which is not above the opening and the distance the force applying means moves to contact the film as compared to the distance it would have to move to contact the support member adjacent the opening may provide a measure of the thickness of the film. Alternatively, a non-contact method, for example, using a laser, may be used for determining thickness of some types of materials.

The puncture test involves the force applying means contacting the centre of the film, above the opening and then moving at a rate of less than 10 mm/minute, preferably less than 5 mm/minute, more preferably less than 2 mm/minute to carry out the puncture test. The force applying means may move at a rate of at least 0.1 mm/minute. Preferably, the test material is stationary and the force applying means moves.

The force applying means penetrates the test material and the method involves taking force and extension measurements during penetration The method may involve determining stiffness and toughness (energy to break) of the test material. In some cases, the method may involve undertaking a series of tests on test materials using force applying means (e.g. the probes referred to above), which have differing diameters. This enables the type of loading applied to the test materials to be varied from bending (in which the upper surface of the test material experiences compression while the lower surface is put under tensile loading) to shear loading as the diameter of the force applying means (in the region which contacts the test material) increases and approaches the diameter of said opening below. The force applying means could be used to make electrical measurements on contacting the test material. This may be useful for investigating conductive adhesives. In impact testing, said force applying means may be moved at high speed towards the test material so that the material is punctured very rapidly. Force measurements are made to assess characteristics of the test material under impact.

In adhesion testing, the method suitably involves contacting the test material with a surface and then moving the force applying means relative to the test material to cause the test material to move away from the surface. In this case, the force applying means may pass into the opening before contacting the test material.

In adhesion testing, the force applying means is moved relatively slowly, towards the stationary test material. The force applying means slowly deforms and/or causes delamination of the test material and the method involves measuring the force applied and distance travelled by the force applying means. The energy per unit area (ie the energy to delaminate a unit area of adhesive) may be determined which is a measure of adhesive strength. Alternatively, rather than determining absolute values, the method may be used to rank a series of test materials.

Preferably, said method according to said first aspect involves testing a plurality of test materials. In this case, the method comprises:

(a) providing a plurality of test materials across respective regions of said support member which are arranged to define respective openings;

(b) moving a said force applying means relative to each test material to apply a respective force to each material;

wherein said force applying means moves towards, passes into and/or passes through each said opening prior to, during or after applying a said force to a respective test material.

Preferably, said regions of said support member are substantially identical to one another. Preferably, in the method, said force applying means applies a force to each of said plurality of test materials in substantially the same manner.

Said support member may include at least 6, preferably at least 10, more preferably at least 15 regions across which test materials are arranged. Said support member preferably defines an array of said regions which regions are preferably arranged in parallel rows. Said support member may be in the form of a well plate in which said regions are defined.

Preferably, the method includes the step of the same force applying means applying a respective said force to each of said plurality of test materials in turn. Thus, the method preferably includes said force applying means applying a force to a first material of said plurality of test materials; and then said force applying means moves relative to said test materials so that it can apply a force to a second material of said plurality of test materials. Although the force applying means itself could move between said first and second materials, the method preferably includes the step of moving said support member to enable said force applying means to apply said force to first and second materials as described. Suitably, said support member is arranged to move (in the direction of an x-y plane (e.g. substantially horizontally) in the method in order to allow the force applying means to apply said force (suitably in a z direction perpendicular to the x-y plane, e.g. vertically) to said plurality of test materials. Preferably, in the method, the force applying means is not moved in said x-y plane (e.g. horizontally) between the application of respective forces to said first and second materials.

Preferably, the method involves recording data relating to each test material in a database.

Preferably, a computer controls the movement of said force applying means relative to each test material. Preferably, the computer is programmed to accurately position the force applying means so that it may apply a force to a test material and pass centrally towards, into and/or through the opening. The method suitably involves the use of a positioning method to achieve this.

The positioning method may involve real-time centring with accurate detection of the opening, for example using a camera and/or a technique using electromagnetic waves.

The positioning method may involve the computer storing a map of said support member that suitably includes the position of each opening and may include the position of one or more reference markers on the support member. In one embodiment, the support member may be very accurately manufactured so that the position of each opening is accurately predetermined. In an alternative embodiment, before any support member is used in the testing of materials, it may be mapped in a mapping procedure.

The mapping procedure preferably includes the steps of recording coordinates for the centres of each opening and assessing the depth of each opening below a surface, for example an upper surface of the support member. For example, when the support member defines a plurality of receptacles, as is preferred, the depths of the receptacles may be determined. The mapping procedure may involve recording coordinates for one or a plurality of reference markers on the support member.

The mapping procedure preferably involves the force applying means moving relative to the support member to contact the support member to enable said coordinates to be determined. Said force applying means preferably moves in the direction of a z axis (e.g. vertically) as described. Additionally, the mapping procedure preferably involves said support member being moved so that different areas thereof are presented to the force applying means to be contacted by said means thereby to map said support member.

After a support member has been mapped, it may be used in testing a material as described. In this case, the support member is selected; the map of the member is called up on the computer; and then the computer controls movement of the force applying means and/or support member to position the aforesaid with respect to reference points on the support member. The centres of the openings (which determines the required x-y positions of the force applying means relative to the support member during a test) are then taken from the stored map enabling the force applying means to be positioned above the centres of the regions which define openings and the method can then be carried out. The method may include the step of measuring the thickness of each test material supported on the support member.

According to a second aspect of the invention, there is provided apparatus for testing a material, the apparatus comprising:

(i) a support member which is arranged to define one or a plurality of openings, wherein said support member is arranged to support test materials;

(ii) a force applying means which is movable relative to the support member for applying a force to a test material supported therein in use;

wherein said force applying means is arranged to move towards, to pass into and/or to pass through said one or plurality of openings in use prior to, during or after applying a force to the test material.

Said apparatus is preferably for carrying out the method described above and may have any feature described above utilized in carrying out said method.

Said support member is preferably movable in the x-y direction suitably in a horizontal plane, for positioning the opening(s) relative to the force applying means. Said force applying means may be movable in the z direction, perpendicular to an x-y plane (e.g. preferably substantially vertically), to apply said force.

Said apparatus preferably includes a computer. Said computer preferably includes an output for controlling movement of the force applying means relative to the support member; and an input for receiving data relating to the force applied and the reaction of the test material to the force applied. Said computer preferably controls the movement of the support member and said force applying means. A database of parameters is preferably associated with said computer. Said database preferably includes coordinates for each opening associated with said support member. Said computer is preferably arranged to control movement of the support member according to said coordinates stored in said database to enable said force applying means to apply a force to a test material.

Said apparatus preferably includes first measurement means for measuring the force applied by said force applying means and preferably includes second measurement means for measuring the distance travelled by said force applying means during a test. Said first and second measurement means are preferably arranged to communicate with said computer and/or database so that measurements taken can be stored.

Said database preferably includes means for storing information relating to the identity of each test material tested using the apparatus. The information stored may include details on the chemical identity of the test materials and/or processes used in their preparation.

In a preferred embodiment, said support member comprises a well plate which includes an array of receptacles each of which includes a respective said opening into and/or through which said force applying means is arranged to pass in use. The apparatus is preferably arranged to test materials positioned in each receptacle.

Any feature of any aspect of any invention or embodiment described herein may be combined with any feature of any aspect of any other invention or embodiment described herein mutatis mutandis.

Specific embodiments of the invention will now be described, by way of example, with reference to the accompanying diagrammatic drawings, in which.

In the Figures, the same or similar parts are annotated with the same reference numerals.

Figure 1:
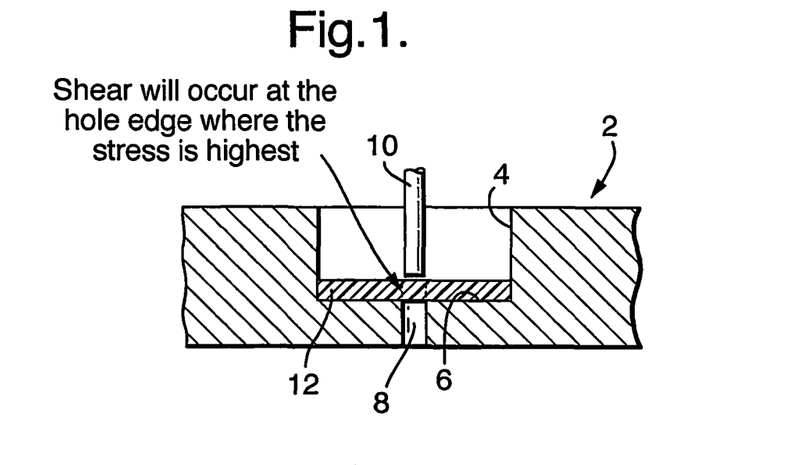
FIG. 1 is a schematic view of apparatus for carrying out a puncture screen.

Referring to FIG. 1, apparatus for testing a film comprises a well plate 2 in which a well 4 is arranged. A base wall 6 of the well 4 includes a circular cross-section channel 8 which is arranged to accommodate an indentor 10 which is used to apply a force to a film 12, positioned in the well 4, to indent and puncture the film. The apparatus is able to make very accurate force measurements that can be used to calculate various physical properties of the film.

Figure 2:
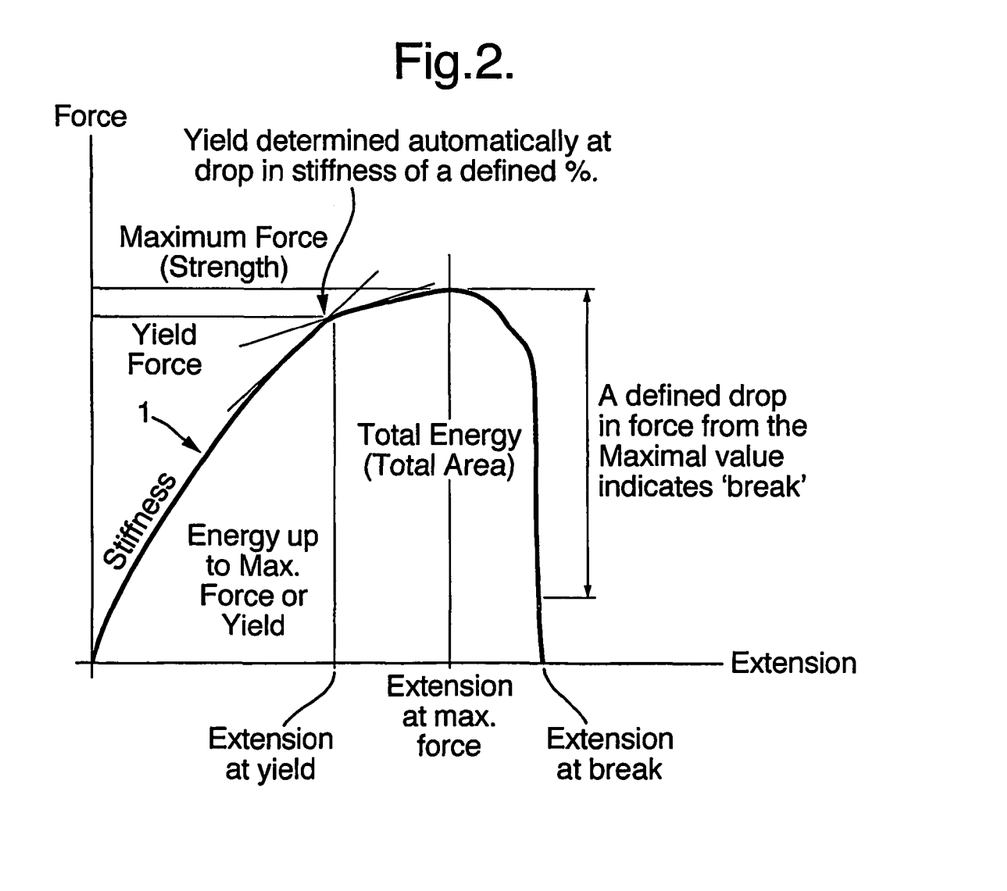
FIG. 2 is a schematic representation of the force extension curve obtained from a typical puncture screen.

The apparatus described may be used to undertake both an indentation screen and a puncture screen of films and a force-extension curve may be constructed as shown in FIG. 2. In this regard, the indentor 10 initially contacts the film 12 and is moved downwardly at a rate of the order of 1 to 2 mm/minute to indent the film. Advantageously, since the film is not supported on a hard substrate (which is often the case in indentation tests) the force is directly related to properties of the film. During movement of the indentor, the force and the displacement are measured and the results can be used to assess the stiffness (slope of the initial part of the curve as indicated by the reference numeral 1 in FIG. 2) of the force/displacement curve which is a system property and a function of geometry which is suitable as a comparator for use in screening materials and through finite element analysis (FEA) leads to material properties.

Figure 3A:
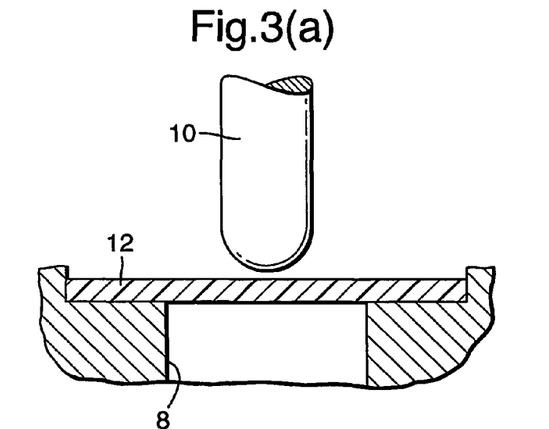
FIGS. 3(a) and 3(b) are a section view and plan view respectively of an indentor contacting a film to illustrate bi-axial loading.
Figure 3B:
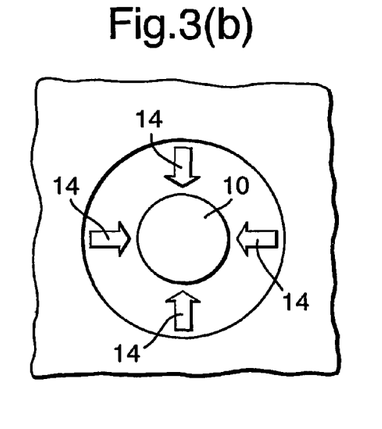

The movement of the indentor is continued to assess the toughness of the film by measuring the energy required to puncture the film. Since the film thickness influences the toughness value, the thickness is recorded to allow normalisation of results. A stiffness value can also be derived from the data acquired from the puncture test. The nature of the stress imposed on the film is determined by the cross-sectional area of the indentor 10 relative to that of the channel 8—the closer the two are in size, the greater the ratio of shear to tensile stress component. Since the position of the indentor within the hole also influences the stress imposed on the film, the indentor should be axially aligned with the centre of the channel 8 during the test to prevent variations of results between different test samples. Such alignment results in "biaxial loading" of the film as represented in FIGS. 3(a) and (b). If, for example, a 350 μm diameter indentor 10 is used to indent/puncture a film of 80 μm nominal (or any) thickness, a biaxial stress field is generated as represented by arrows 14.

Using indentors of different diameters also allows the type of loading to be changed from bending (in which the upper surface of the film 12 experiences compression while the lower surface is put under tensile loading) to shear loading as the indentor diameter increases and approaches the diameter of the channel below. This may have application in testing materials that require their shear behaviour to be measured.

FIG. 2 details a number of parameters that may be obtained from the force-extensive curve to allow different films tested to be compared.

The indentor 10 is controlled by a Universal Testing Machine, for example an Instron MicroTester (Trade Mark) obtained from Instron of Massachusetts, USA. The instrument is capable of vertical movement (z axis) to within a micron accuracy and very sensitive force measurements (nominally accuracy is as good as 0.5 mN provided the instrument is isolated from mechanical noise). The Instron instrument includes a software package (Merlin (Trade Mark)) which enables the Instron MicroTester to be controlled and data to be acquired and stored.

Figure 4:
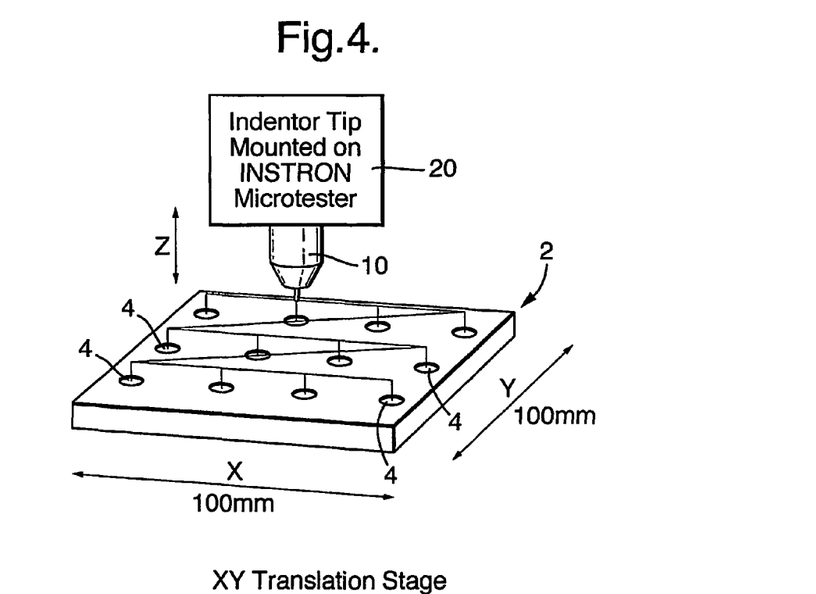
FIG. 4 is a schematic representation of apparatus for carrying out high-throughput testing of films.

The apparatus described above may be configured for the high-throughput screening of films. This is illustrated schematically in FIG. 4. Referring to FIG. 4, well plate 2 includes an array of wells 4 (only some of which are shown in FIG. 4) in which films may be arranged. The well plate 2 is mounted on an x-y translation stage (not shown) which is arranged to move the well plate so that each well 4 may be positioned underneath the indentor 10 of the Instron Microtester which is arranged in a fixed x-y position. The x-y translation stage was a Newport (Trade Mark) x-y stage obtained from Newport Ltd that is capable of 1 μm positional resolution (4 μm positional accuracy) and a total movement of 200 by 100 mm so that it may tranverse all samples in the array. The indentor 10 can then move in the z-direction as described above to contact and test films in the wells. The movement of the Instron MicroTester and the x-y stage are controlled by software and any reference points, test positions and results are stored in a database.

As described above with reference to FIG. 3, to achieve accurate reproducible results, the indentor 10 needs to be axially aligned with the centre of the channel 8. A first step involved in achieving this is to map a plate to be used (e.g. plate 2 of FIG. 5), as follows:

First a new entry is made in the database with the nominal positions of all required reference and test positions. Then the actual positions are measured. In the first stage of this process, the software directs the Instron MicroTester and x-y stage to measure the height (z value) of several predefined reference points on the surface plane 22 of the well plate 2 (for example a part of diagonally arranged reference points may be addressed). The positions of the reference holes (eg 21 in FIG. 5) are then determined using their nominal positions (all input prior to the start) and a centre detection algorithm to refine the supplied co-ordinates.

Figure 5:
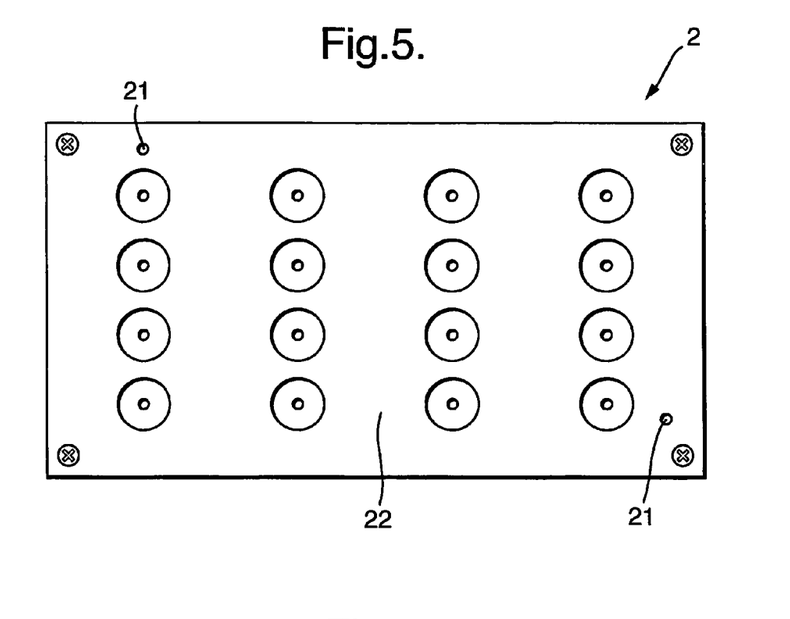
FIG. 5 is a top plan view of a 4×4 well plate.

The centre detection algorithm finds the centre and radius of the holes/channels by identifying three or more points on the circumference of a hole/channel. These can be found by conducting a series of surface height measurements, at various x-y positions (which are calculated systematically by the software) in the area where the hole/channel is known to be. The first measurement is the surface height around the hole/channel (for reference in the hole detection and to provide well depth information). Subsequent surface height positions, in conjunction with surface and well floor height information, allow the software to identify those x-y positions where the indentor goes into the hole/channel. Points on the circumference of the hole can be identified by seeking transitions from 'in' to 'outside' of the hole/channel. Once a transition is found, its position is refined by making further surface position measurements between the known 'in' and 'out' points until the position is known to within a predefined accuracy (the accuracy limit is dependent on the x-y stage positioning accuracy). Once sufficient points have been identified, a least squares fit is employed to determine the centre and radius of the hole/channel. Validity is checked by comparing the measured radius to the nominal value and further points may be measured to improve the fit if required.

The position and radius of every reference hole and channel may be measured as described.

Usually two reference holes are present at the top left and bottom right corners of the well plate. The origin of the co-ordinate system is reset to the measured centre position of a nominated reference hole. The depths of the wells are determined relative to a least squares fit of the surface plane.

All of the data collected in the manner described makes up a unique "plate definition" which is stored in the database. Unique plate definitions may be determined for a number of plates.

After a "plate definition" has been determined for a particular plate, the plate can be used in the high-throughput screening of films. At the start of the screening, the plate definition for the particular plate chosen is selected from a list stored in the database and the user is asked to approximately position the indentor tip over each reference hole in turn. The software then determines the position of the surface plane of the plate and locates the centre of the nominated reference hole. The co-ordinate system is then corrected for any rotation by comparison of the position of the reference holes (not including the origin point) in the stored plate definition and the new measurement. The centres of the channels can then be looked up in the database from the stored plate definition.

A wide range of types of films may be investigated: for example, a series of polyurethane/acrylic dispersions may be prepared in a combinatorial technique and data relating to the preparation stored in a database so that each film can be identified. In one embodiment, a predetermined amount of each liquid dispersion may then be pipetted into a selected well 4 in the well plate 2 and, optionally, the well plate 2 may be oscillated gently to facilitate consistent film formation. Each film 12 is formed over a channel 8 as represented in FIG. 3(a). It will be appreciated that the diameter of channel 8 and the material from which the well plate 2 is made (particularly in the area around the channels 8) will affect formation of the film and whether it extends across the channel as shown in FIG. 3(a) or sags into the channel. Suitably, the well plate 2 is optimised to reduce the tendency of the film to sag into the channel and, therefore, aid the collection of accurate test results. The amount of sag is determined during testing and if it is greater than 15% of the thickness of the film, the results from the testing of the film are discarded.

After respective films have been formed, the thickness of them may be determined. As described above, during mapping of the well plate, the surface plane of the plate is identified (by a least squares fit on several surface position measurements) and the position of the floor in each well is measured. This allows the well depths to be calculated by simple subtraction. To determine the film thickness, the well depths are re-measured in a similar way and since the floor position will be higher by the thickness of the film, a comparison of the well depths with and without films will yield the film thickness.

Next, each film may be addressed in turn, under computer control, by the software causing the x-y stage to move so that the indentor 10 is positioned centrally above a selected channel 8. Then, the indentor moves downwardly to contact and test the film 12 as described above and the results are used to calculate properties of the film. The x-y stage then positions each channel accurately below the indentor in turn and each film is tested as described.

As an alternative to mapping plates and then the computer using the map to position the Instron Microtester over the centres of channels 8, accurately manufactured plates wherein the centres of the channels are known may be used. Alternatively, machine vision may be used. In this case, an image of each channel 8 is acquired using a camera and image analysis software is used to derive size and positional information. Since the camera will need to be offset from the indentor 8, the respective relative positions of camera and indentor must be accurately known so that the position of the channel relative to the indentor can be calculated.

Figure 6:
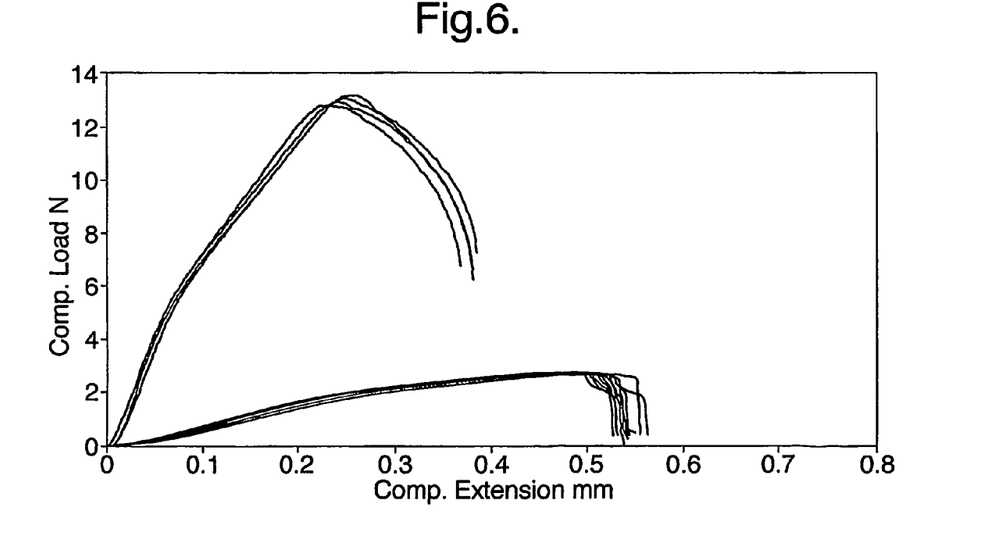
FIG. 6 is a graph of force vs. extension for two materials.

After each film has been tested, the database will store all relevant information on each film, for example, relating to the process for its preparation; the materials used in its preparation; its thickness; and the results of the indentation and puncture tests which enable physical properties of the film to be determined. A force-extension curve may be produced as shown in FIG. 2. Also, materials may be compared as shown in FIG. 6

Figure 7A:
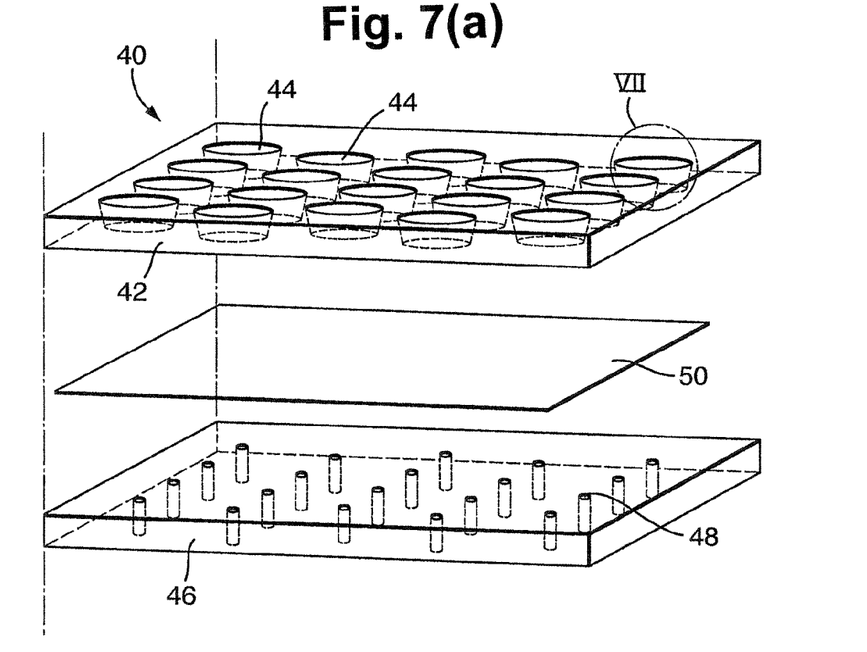
FIG. 7a is an exploded perspective view of a clamping device for free standing films.
Figure 7B:
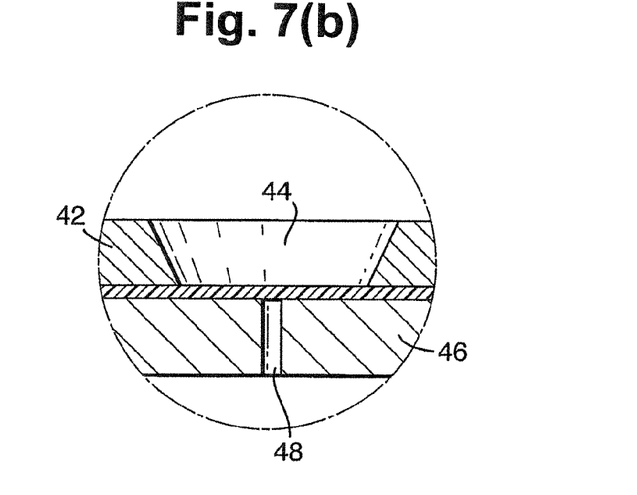
FIG. 7b is an enlarged cross-sectional view of circled region VII in FIG. 7a with the clamping device assembled.

Preformed films of materials may be evaluated using the clamping device shown in FIG. 7. Referring to FIG. 7, the device 40 includes an upper clamping plate 42 in which an array of inwardly tapering openings 44 are defined, and a lower clamping plate 46 in which an array of narrower cylindrical openings 48 are defined. The centre of each opening 48 is aligned with the centre of a respective opening 44. A film 50 to be evaluated is clamped between upper and lower plates 42, 46, with the plates being secured by bolts (not shown) that extend therethrough. An indentor 10 may then be used to test the film as described above.

As described above, it is preferred to minimise any sag of films into the channels in the well plate. Some film materials may have a greater tendency to sag than others. In this case, the apparatus and process for preparing the films may be modified as described below with reference to FIG. 8.

Figure 8A:
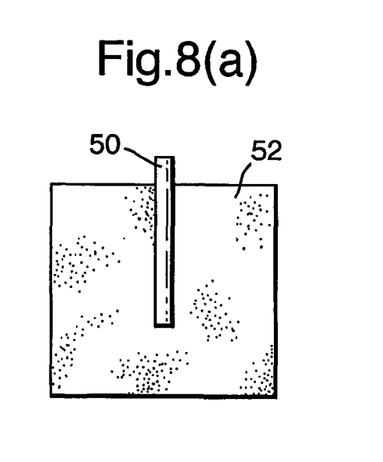
FIGS. 8(a) to (d) show steps in plugging channels in a well plate to facilitate film formation.
Figure 8B:
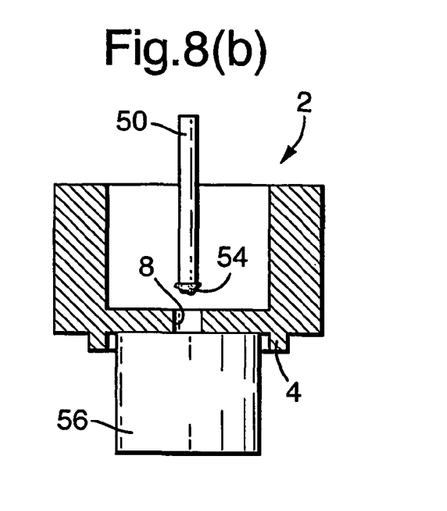
Figure 8C:
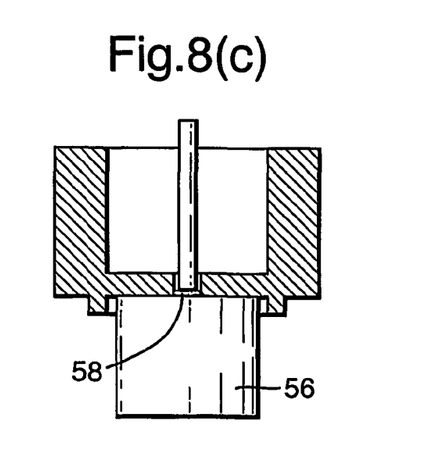
Figure 8D:
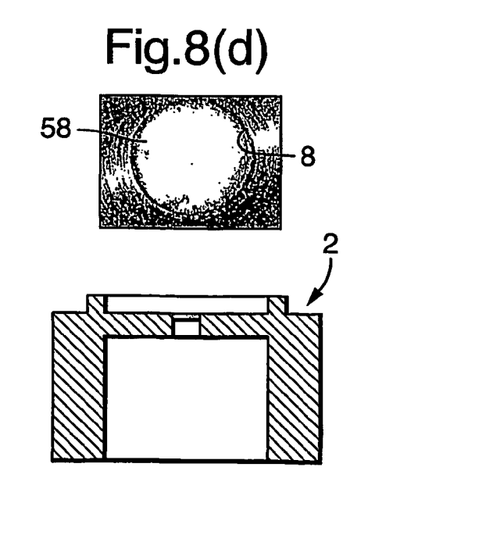

FIG. 8(a) shows a rod 50 being dipped into PTFE powder 52 so that a small amount 54 of the powder can be picked up on the end of the rod as shown in FIG. 8(b). FIG. 8(b) shows parts of an inverted well plate 2 in which a well 4 and circular cross-section channel 8 are defined. A stopper 56 is used to close the channel 8 and then the rod is inserted into channel 8 and used to position and compact the powder against the stopper 56 to define a plug 58 which closes the channel, as shown in FIG. 8(c). The well plate 2 may be returned to its normal position as shown in FIG. 8(d) whereupon it is ready for a film to be cast over the channel 8. FIG. 8(d) also shows a plan view micrograph of a plug 58.

The identity of the powder (e.g. PTFE), the particle sizes, and the amount used in channel 8 are selected so that the powder will support the film during its formation and prevent sag into the channel. Nonetheless, when the film is indented and/or penetrated by the indentor 10, the powder can fall from the channel on application of a relatively small force. Thus, the presence of the powder will not affect significantly the validity of the test results achieved using the Instron MicroTester and/or the test results can be adjusted to take into consideration the presence of the PTFE, if necessary.

The use of indentation and puncture testing as described above has shown advantages over conventional tensile techniques and is particularly evident for reproducibility. Tensile testing of fracture mechanics measurements for delicate film specimens requires meticulous specimen preparation, especially from films. Brittle films are particularly prone to variability in the quality of the free edges of specimens, from which failures can be initiated if notches are present. In ductile films this can promote local yielding due to stress concentration, and this leads to high levels of scatter in the yield and post yield behaviour.

However, in the methods described, whether the film is clamped in place and held over a hole by a clamping plate (for free standing film) shown in FIG. 7, or by casting the film in a well plate (FIGS. 1, 3, 4, 5 and 8), there are no free edges from which to initiate fracture or premature yielding.

Data collected using the methods described shows an extremely high level of reproducibility. Furthermore, data for very brittle films (which would be very difficult to obtain using conventional methods which would necessitate the films to be cast and then positioned in a test apparatus) can be obtained by casting the films in wells and testing the films in the same wells without them being moved to a separate location.

Figure 9A:
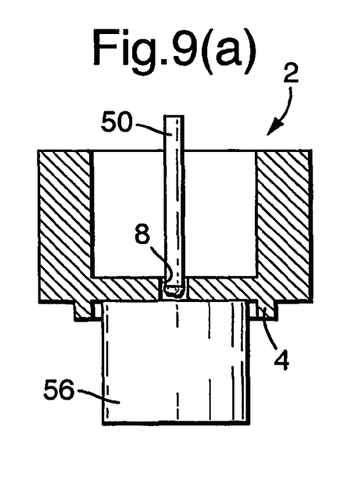
FIGS. 9(a) to 9(c) show the preparation of a well plate for adhesion testing of a material and FIG. 9(d) illustrates an adhesion test.
Figure 9B:
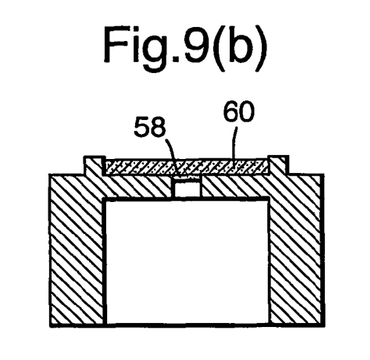
Figure 9C:
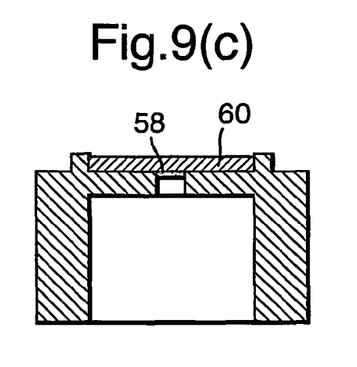
Figure 9D:
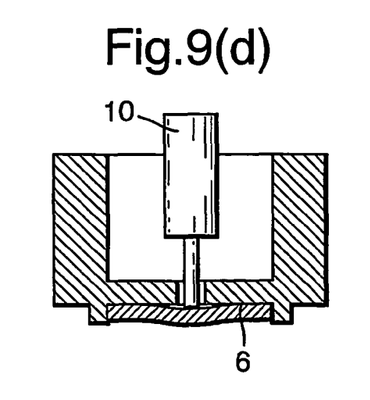

FIGS. 9(a) to (d) show the steps involved in carrying out an adhesion screen of a material. FIG. 9(a) shows the closing of channel 8 with PTFE which is accomplished as described with reference to FIGS. 8(a) and (b). The well plate 2 (which in this case is made of an appropriate material against which an adhesive material is to be assessed) is returned to its normal position as shown in FIG. 9(b) and the well is filled with a candidate adhesive 60 which is cured or conditioned thereby to define a test material (FIG. 9(c)). The well plate 2 is then inverted as shown in FIG. 9(d) and indentor 10 is moved downwardly to contact the plug 58 thereby to apply a force to the adhesive to cause it to pull away from base wall 6. During the test, the force applied and the distance travelled by the indentor are monitored and data recorded in a database. From data recorded, characteristics of the adhesive may be determined.

In some cases, there may be a risk that indentor 10 may puncture the adhesive rather than delaminate it. To overcome this, a reinforcing material, for example a foil, may abut and be positioned below (with reference to FIG. 9(d)) the adhesive to promote adhesive failure rather than puncturing.

Apparatus (not shown) but similar to that used in the puncture test may be used in the impact testing of a material. The test involves causing an indentor 10 to contact a test material at high speed to penetrate it and undertaking relevant measurements during the test.

The invention claimed is:

1. A testing apparatus, comprising:
    (a) a support member, comprising:
        i) a first side and an opposing second side, wherein said first side comprises at least one receptacle having an opening and a base that define a test sample area;
        ii) said base comprising at least one opening defining an axially-uniform channel, wherein said channel is in communication with both the test sample area and said second side;
        iii) said at least one receptacle and said at least one opening defining said channel each having a central-vertical axis; and
    (b) at least one probe having a central-vertical axis and a distal end, said at least one probe arranged above said at least one receptacle such that the central-vertical axis of said at least one probe is substantially aligned with the central-vertical axis of said at least one opening defining said channel, and said at least one probe is capable of being moved upwardly and downwardly substantially in-line with the central-vertical axis of said at least one probe such that said distal end of said at least one probe is able to enter said at least one opening in said base.

2. The apparatus of claim 1, wherein the opening in said base is smaller than the opening in said at least one receptacle.

3. The apparatus of claim 1, wherein the central-vertical axis of said at least one receptacle is substantially aligned with the central-vertical axis of said at least one opening in said base.

4. The apparatus of clam 1, wherein said support member comprising at least one further receptacle having an opening and a base that define a further test sample area, said base comprising at least one opening in communication with the further test sample area, and said at least one receptacle and said at least one opening each having a central-vertical axis.

5. The apparatus of claim 4, wherein said support member is capable of being moved in a plane perpendicular to the central-vertical axis of said at least one probe such that said support member can be moved from a position wherein the central-vertical axis of said at least one receptacle is aligned with the central-vertical axis of said at least one probe to a position wherein the central-vertical axis of said at least one further receptacle is aligned with the central-vertical axis of said at least one probe.

6. The apparatus of claim 1, wherein the opening in said at least one opening in said base comprises a temporary plug that does not substantially protrude into the test sample area.

7. The apparatus of claim 6, wherein said temporary plug is composed of a compressed particulate.

8. The apparatus according to claim 1, further comprising a computer.

9. The apparatus according to claim 8, wherein said computer includes an output for controlling movement of the said at least one probe relative to the support member; and an input for receiving data relating to a force applied.

10. The apparatus according to claim 1, wherein said at least one receptacle comprises an array of receptacles, each of which includes a respective said opening into and/or through which said at least one probe is arranged to pass in use.

11. A method of testing a material comprising:
    (a) placing a sample of a test material in at least one receptacle of an apparatus comprising:
        (1) a support member comprising said at least one receptacle having an opening and a base that define an area for receiving the test sample;

i) said base comprising at least one opening in communication with the area defined for receiving the test sample;
ii) said at least one receptacle and said at least one opening in said base each having a central-vertical axis; and
(2) at least one probing element having a central-vertical axis and a distal end, said at least one probing element arranged above said at least one receptacle such that the central-vertical axis of said at least one probing element is substantially aligned with said central-vertical axis of said at least one opening in said base;
(b) re-positioning said at least one probing element downwardly, substantially along the central-vertical axis of said at least one probing element, in through the opening in said at least one receptacle and to a position such that the distal end of said at least one probing element is proximate a surface of the test material; and
(c) temporarily plugging said at least one opening in said base by compressing a particulate material.

12. A method according to claim 11, which includes recording a force applied to said test material or a parameter relating to the force applied by said at least one probing element.

13. A method according to claim 12, wherein a multiplicity of values for the force applied to said test material are recorded at different times during the testing of said material.

14. A method according to claim 12, wherein data relating to the force applied is recorded in a database under the control of a computer and said computer also controls the movement of said at least one probing element relative to said test material.

15. A method according to claim 11, wherein said at least one probing element applies a force that deforms the test material.

16. A method according to claim 11, which includes moving the at least one probing element to apply a force to said material.

17. A method according to claim 16, wherein said test material is stationary during application of said force.

18. A method according to claim 11, which includes the step of constructing a force vs extension relationship for the test material or a tensile stress vs tensile strain relationship for the test material.

19. A method according to claim 11, wherein the test material is arranged across said at least one opening in said base.

20. A method according to claim 19, wherein said test material is preformed.

21. A method according to claim 11, wherein said at least one opening in said base is closed by a plug means prior to the test material being tested.

22. A method according to claim 11, wherein a precursor of the test material is selected and contacted with said support member, said precursor being in a different physical form compared to said test material, wherein said test material forms on said support member after contact of the precursor therewith.

23. A method according to claim 22, wherein said precursor includes at least first and second components which are involved in the formation of the test material.

24. A method according to claim 23, wherein, in a series of tests, the identity, and/or amounts of the first and second components are varied; and/or the processes to which the first and second components are subjected are varied;
and/or the identity and/or amounts of other components are varied, with a view to affecting the properties of the test materials formed.

25. A method according to claim 11, which is a method of puncture testing, impact testing or adhesion testing.

26. A method according to claim 25, wherein a method of puncture testing includes the step of moving said at least one probing element relative to the test material so that at least a portion of said at least one probing element penetrates the test material, wherein force and extension measurements are made during the penetration.

27. A method according to claim 25, wherein a method of adhesion testing involves contacting the test material with a surface and then moving the at least one probing element relative to the test material to cause the test material to move away from the surface.

28. The method according to claim 11, wherein said computer controls the movement of the support member and said at least one probing element.

29. The method according to claim 11, said apparatus including first measurement means for measuring a force applied by said at least one probing element and second measurement means for measuring the distance traveled by said at least one probing element during a test.

30. The method according to claim 29, wherein said first and second measurement means are arranged to communicate with a computer which includes means for storing information relating to the identity of each test material tested using the apparatus and means for storing measurements taken.

31. The method of claim 11, wherein said at least one probing element is re-positioned such that at least the distal end of said at least one probing element contacts said test material at a position proximate the central-vertical axis of said at least one opening in said base.

32. A method of testing a material comprising:
(a) placing a sample of a plurality of test materials in receptacles of an apparatus comprising:
(1) a support member comprising an array of receptacles arranged in parallel rows each having an opening and a base that define an area for receiving the test sample, each said base comprising at least one opening in communication with the respective area defined for receiving the test sample, each of said array of receptacles and each of said at least one opening in said base each having a central-vertical axis;
(2) at least one probing element having a central-vertical axis and a distal end, said at least one probing element arranged above at least one of receptacle within said array of receptacles such that the central-vertical axis of said at least one probing element is substantially aligned with said central-vertical axis of said at least one opening in said base of said at least one receptacle,
(b) re-positioning said at least one probing element downwardly, substantially along the central-vertical axis of said at least one probing element, in through the opening in said at least one receptacle and to a position such that the distal end of said at least one probing element is proximate a surface of said sample; and
(c) temporarily plugging said at least one opening in said base by compressing a particulate material.

33. A method according to claim 32, wherein the same said at least one probing element is used to apply a force to each of said plurality of test materials in turn.

34. A method according to claim 32, which includes the step of moving said support member to enable said at least one probing element to apply a force to a first sample and a second sample of said plurality of test materials each in separate receptacles within said array of receptacles included in said plurality of test materials.

35. A method according to claim 34, wherein the movement of said at least one probing element is controlled by a computer.

* * * * *